United States Patent
Siebecke et al.

(10) Patent No.: US 9,561,999 B2
(45) Date of Patent: Feb. 7, 2017

(54) METHOD FOR THE PRODUCTION OF AN AQUEOUS SOLUTION OF SALTS

(75) Inventors: Ekkehard Siebecke, Berlin (DE); Mirko Bär, Birkenwerder (DE); Eberhard Raue, Schönfließ (DE)

(73) Assignee: UHDE INVENTA-FISCHER GMBH, Berlin (DE)

( * ) Notice: Subject to any disclaimer, the term of this patent is extended or adjusted under 35 U.S.C. 154(b) by 114 days.

(21) Appl. No.: 14/131,855

(22) PCT Filed: Jun. 5, 2012

(86) PCT No.: PCT/EP2012/060616
§ 371 (c)(1),
(2), (4) Date: May 2, 2014

(87) PCT Pub. No.: WO2013/007451
PCT Pub. Date: Jan. 17, 2013

(65) Prior Publication Data
US 2014/0249330 A1 Sep. 4, 2014

(30) Foreign Application Priority Data
Jul. 11, 2011 (EP) .................. 11005653

(51) Int. Cl.
*C07C 55/14* (2006.01)
*C07C 51/14* (2006.01)
(Continued)

(52) U.S. Cl.
CPC ............. *C07C 209/68* (2013.01); *B01J 8/20* (2013.01); *C07C 51/412* (2013.01);
(Continued)

(58) Field of Classification Search
CPC .......... C07C 209/68; C01C 51/412; B01J 8/20
(Continued)

(56) References Cited

U.S. PATENT DOCUMENTS 3,496,133 A     2/1970  Hoffman
4,233,234 A *  11/1980  Rotzoll et al. ............... 562/590
(Continued)

FOREIGN PATENT DOCUMENTS

DE    16 04 368 A1   9/1970
DE    21 39 642 A1   2/1973
(Continued)

OTHER PUBLICATIONS

Mexican Institute of Intellectual Propery, Office Action in Mexican Patent Application No. MX/a/2013/014975, Aug. 13, 2015, 4 pp.
(Continued)

*Primary Examiner* — Kamal Saeed
*Assistant Examiner* — Janet L Coppins
(74) *Attorney, Agent, or Firm* — Leydig, Voit & Mayer, Ltd.

(57) ABSTRACT

The invention relates to a method for the continuous production of a solution of salts, in particular for the production of hexamethylenediamine adipate and a device for implementing such a method. According to the invention, it is proposed to convert, in a first step, a substoichiometric quantity of alkane diamine in a ratio to the alkane dicarboxylic acid in water and, in a subsequent second step, to implement making-up with alkane diamine, adjustment of the stoichiometric ratios being effected via a pH value measurement at a constant temperature.

20 Claims, 4 Drawing Sheets

(51) Int. Cl.
  *B01J 8/20* (2006.01)
  *C07C 209/68* (2006.01)
  *C07C 51/41* (2006.01)
(52) U.S. Cl.
  CPC .............. *B01J 2208/00592* (2013.01); *B01J 2208/00628* (2013.01); *B01J 2219/0004* (2013.01)
(58) Field of Classification Search
  USPC ........................................................ 562/590
  See application file for complete search history.

(56) References Cited

U.S. PATENT DOCUMENTS

| | | | |
|---|---|---|---|
| 5,376,702 | A | 12/1994 | Stibal et al. |
| 5,458,478 | A | 10/1995 | Stibal et al. |
| 5,703,204 | A | 12/1997 | Gittinger et al. |
| 2010/0168375 | A1* | 7/2010 | Thierry ............... C07C 51/412 528/335 |
| 2010/0237521 | A1 | 9/2010 | Deiss |
| 2012/0046439 | A1 | 2/2012 | Lomel et al. |
| 2014/0243473 | A1 | 8/2014 | Siebecke et al. |
| 2014/0249330 | A1 | 9/2014 | Siebecke et al. |
| 2015/0314969 | A1 | 11/2015 | Siebecke et al. |
| 2016/0001254 | A1 | 1/2016 | Siebecke et al. |
| 2016/0032050 | A1 | 2/2016 | Siebecke et al. |

FOREIGN PATENT DOCUMENTS

| | | |
|---|---|---|
| DE | 40 39 857 A1 | 4/1992 |
| DE | 102007057189 A1 | 6/2009 |
| EP | 0 000 158 A1 | 1/1979 |
| EP | 0 000 397 | 1/1979 |
| EP | 0 122 005 A1 | 10/1984 |
| EP | 0 745 631 A1 | 12/1996 |
| JP | 2010-529066 A | 8/2010 |
| WO | WO 2010/115727 A1 | 10/2010 |

OTHER PUBLICATIONS

Japanese Patent Office, Office Action in Japanese Patent Application No. 2014-519469, Sep. 2, 2015, 6 pp.
Eise et al., "Compounding of Additives and Fillers," *Chemical Engineering Progress*, 78:1, pp. 62-64 (1982).
Lückert et al., "Neuartige wirtschaftliche Technologien zur Produktion von PEF-Fasern," *Chemiefasern and Textilindustrie* 36:88 ("New commercial technologies for the production of PES fibres," *Chemical Fibres and Textile Industry* 1), pp. 24-29 (1986).
"Chemisches Gleichgewicht," Wikipedia, der freien Enzyklopädie, retrieved from the Internet: URL http://de.wikipedia.org/wiki/Chemisches_Gleichgewicht [retrieved on Jan. 12, 2012] (6 pgs.).
European Patent Office, International Search Report in International Application No. PCT/EP2012/060616 (Jul. 10, 2012).
European Patent Office, Written Opinion in International Application No. PCT/EP2012/060616 (Jul. 10, 2012).
European Patent Office, International Preliminary Report on Patent ability in International Application No. PCT/EP2012/060616 (Jul. 30, 2013).
State Intellectual Property Office of the People's Republic of China, Notification of the First Office Action in Chinese Patent Application No. 201280032561.9 (Jan. 27, 2015).
Japanese Patent Office, Notification of Reasons for Refusal in Japanese Patent Application No. 2014-519469 (Sep. 9, 2015).
U.S. Appl. No. 14/124,296, filed May 13, 2014.
U.S. Appl. No. 14/762,105, filed Jan. 20, 2014.
U.S. Appl. No. 14/767,812, filed Feb. 24, 2014.
U.S. Appl. No. 14/766,045, filed Jan. 20, 2014.
Taiwan Intellectual Property Office, Notice of Examination in Taiwanese Patent Application No. 101121479 (Dec. 15, 2015).
Federal Institute of Industrial Property, Official Action (Inquiry) of the State Examination in Russian Patent Application No. 2013158012/04 (Apr. 15, 2016).

* cited by examiner

METHOD FOR THE PRODUCTION OF AN AQUEOUS SOLUTION OF SALTS

CROSS-REFERENCE TO RELATED APPLICATIONS

This patent application is the U.S. national phase of International Application No. PCT/EP2012/060616, filed on Jun. 5, 2012, which claims the benefit of European Patent Application No. 11005653.8, filed Jul. 11, 2011, the disclosures of which are incorporated by reference.

The invention relates to a method for the continuous production of a solution of salts, in particular for the production of hexamethylenediamine adipate and a device for implementing such a method. According to the invention, it is proposed to convert, in a first step, a substoichiometric quantity of alkane diamine in a ratio to the alkane dicarboxylic acid in water and, in a subsequent second step, to implement making-up with alkane diamine, adjustment of the stoichiometric ratios being effected via a pH value measurement at a constant temperature.

Methods for the continuous production of aqueous solutions of salts of alkane dicarboxylic acids and alkane diamines which are required in particular as starting product for the production of polyamides are known in the state of the art.

Thus EP 0 000 158 B1 describes a continuous method for the production of an aqueous solution of salts of alkane dicarboxylic acids and alkane diamines. The production of the salt solution is achieved accordingly by conversion of the corresponding alkane dicarboxylic acids with the respective alkane diamines in an aqueous solution of the salt respectively to be produced, the aqueous salt solution being guided in a circulation, firstly dicarboxylic acids being converted with alkane diamines in a limited quantity and then the remaining quantity of alkane diamine being added.

A further method for the synthesis of hexamethylenediamine adipate from adipic acid and hexamethylenediamine for the production of nylon 66 is known from EP 0 122 005 B1. In the case of this method, firstly an aqueous solution of the salt is produced and then, in a subsequent method step, concentration of the solution is achieved by evaporation. Finally, it then becomes obvious with this method, in order to compensate for the losses of the hexamethylenediamine during evaporation, implementing making-up of the hexamethylenediamine up to an equimolar ratio of hexamethylenediamine to adipic acid.

However, it was shown here that the methods of the state of the art still do not lead in every respect to a satisfactory result. Thus, in particular the making-up, as is proposed in EP 0 000 158 B1, is difficult. It emerged that no exact stoichiometric composition could consequently be produced.

Also, the method still has disadvantages, as is described in EP 0 122 005 B1, since xthe alkane dicarboxylic acid is used herein as an aqueous solution. Even with this, evaporation losses hence occur during the reaction which are no longer precisely controllable.

Starting herefrom, it is therefore the object of the present invention to propose an improved continuous method for the production of aqueous solutions of salts by conversion of alkane dicarboxylic acids with 6 to 12 carbon atoms and alkane diamine with 6 to 12 carbon atoms. Furthermore, it is an object of the present invention to indicate a corresponding device for this purpose.

The object is achieved, by the features of the method for the continuous production of a solution of salts and the device for implementing the method described herein, and the advantageous developments thereof.

According to the invention, it is hence proposed to obtain the salt solution by metering the alkane dicarboxylic acid as solid material into a first reactor via at least one first feed point and metering in a substoichiometric quantity of undiluted alkane diamine at at least a second feed point, and also, at the same time, water at a third feed point of the first reactor. The consequently formed salt solution is transferred continuously into a subsequently connected second reactor and, in the second reactor, making-up with the alkane diamine is then effected. It is now essential to the invention that the stoichiometric ratios in the first and second reactor are adjusted via a pH value measurement at a constant temperature.

An essential advantage of the method according to the invention resides in the fact that the alkane dicarboxylic acid is introduced as a solid material into the first reactor and hence exact metering of the solid material is possible. The alkane dicarboxylic acid as solid material is thereby preferably metered into the first reactor via a metering device with a gravimetric throughflow measurement. According to the invention, in addition the alkane diamine is introduced, likewise undiluted, into the reactor so that, here also, an exact predetermination of the quantity required for the necessary stoichiometric ratios can be detected exactly. Furthermore, it is thereby essential that water is then supplied, at the same time, in the prescribed quantity into the first reactor with the undiluted alkane diamine in order to produce the corresponding aqueous solution. Adjustment of the stoichiometric ratio is thereby effected via a pH measurement at a constant temperature. The stoichiometric ratios of the alkane dicarboxylic acid to the alkane diamine in the first reactor are thereby adjusted such that they are in the range of 1:0.80 to 0.99, preferably 1:0.85 to 0.99 and particularly preferred 1:0.95 to 0.99. The pressure which is intended to be maintained in the first reactor is in the range of 0.9 to 1.2 bar (absolute) and the temperature in the range of 70 to 120, in particular of 80 to 95° C., very particularly preferred at 90° C.

In the first reactor, the aqueous solution is maintained at a concentration of salts of alkane dicarboxylic acids, alkane diamines of 50 to 65% by weight, particularly preferred in the range of 63% by weight.

In the case of the method according to the invention, the thus produced salt solution is transferred continuously, in a second step, into a subsequent second reactor.

In the second reactor, the process is now such that making-up with the alkane diamine is undertaken there, here also, the stoichiometric ratio being controlled again via a pH value measurement at a constant temperature.

As a result of the fact that now, as proposed in the case of the invention, the process takes place in two steps and, in each individual step, adjustment of the molar ratio of alkane dicarboxylic acid to alkane diamine is effected via a pH value measurement, it can be ensured that, in the case of the method according to the invention, a salt solution of the alkane dicarboxylic acid with the alkane diamine in ideal molar ratios is obtained without evaporation losses thereby occurring or overfeeding of one of the reaction partners being effected. Also, any evaporation losses can be jointly allowed for.

In the case of the method according to the invention, it is favourable in addition if, both in the first reactor and in the second reactor, the supply of the educts, in particular the supply of the alkane dicarboxylic acid, is undertaken in solid form under a protective gas atmosphere.

The method according to the invention can thereby be designed also such that the water and the inert gas for the first and/or second reactor is guided in a circulation.

The method according to the invention can basically be applied to all alkane dicarboxylic acids with 6 to 12 carbon atoms and all alkane diamines with 6 to 12 carbon atoms. Preferred examples of the alkane dicarboxylic acids are adipic acid, octanedioic acid, azeleic acid, sebacic acid, decanedioic acid, dodecanedioic acid and also mixtures hereof. Examples of alkane diamines are hexamethylenediamine, octamethylenediamine, decamethylenediamine, dodecanemethylenediamine, bis(4-aminocyclohexyl)methane and bis(4-aminocyclohexyl)propane-2,2.

Furthermore, the invention relates to a device for implementing the above-described method.

The device is distinguished in particular by two reactors being provided which are connected to each other, the first reactor having separate feed points for the educts. The first reactor according to the invention hence has at least one first feed point for the alkane dicarboxylic acid, at least one second feed point for the alkane diamine and at least one third feed point for the water. The second reactor has at least likewise one feed point for the alkane diamine. Furthermore, the device also has mechanisms for measuring the pH value of the aqueous solution of salts in the first and/or second reactor and a control unit which, by means of the measured pH value, enables making-up of the alkane diamine in the second reactor.

In the case of the reactors, in particular stirred reactors are preferred, which can also be provided with a heating or cooling jacket or else have a heating or cooling device. The reactors can be configured in addition as autoclaves.

BRIEF DESCRIPTION OF THE DRAWINGS

The invention is explained subsequently in more detail with reference to FIGS. 1 to 4.

DETAILED DESCRIPTION OF THE INVENTION

Figure 1:
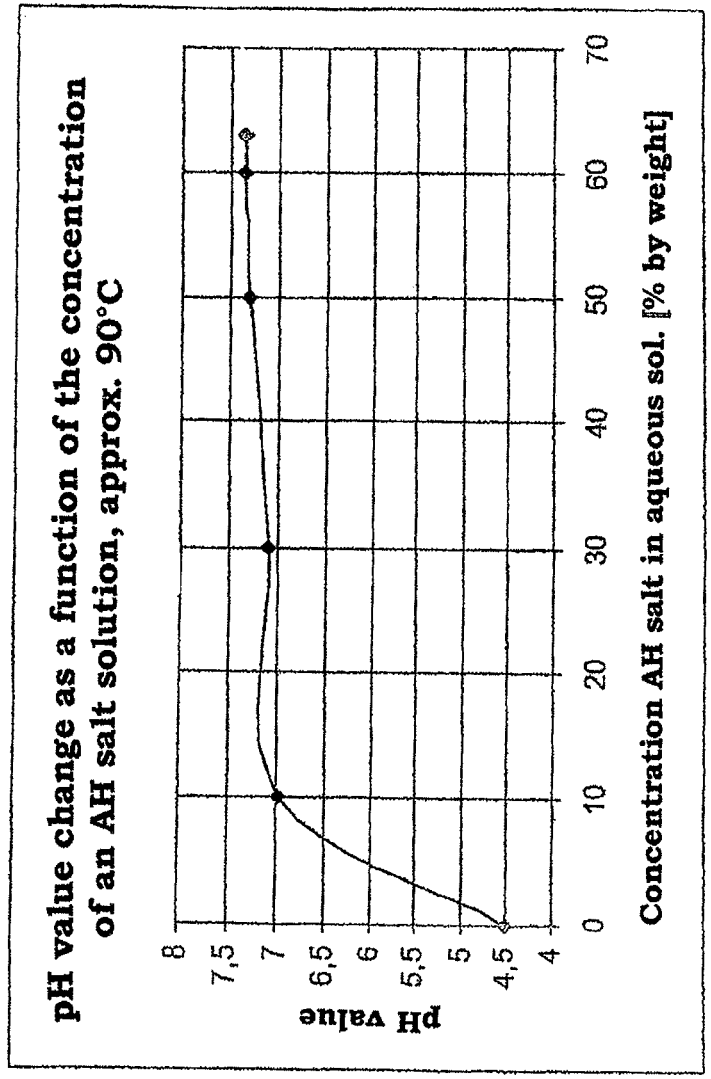
FIG. 1 shows the pH value change as a function of the concentration of an AH salt solution at 90° C.
Figure 2:
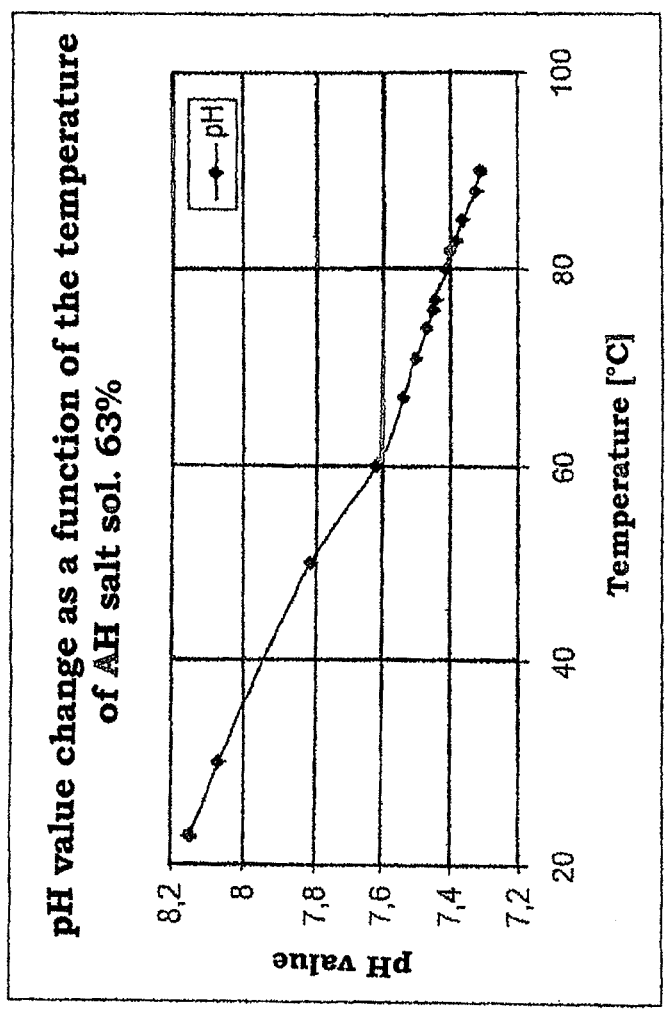
FIG. 2 shows graphically the pH value change as a function of the temperature of an AH salt solution of 63%.
Figure 3:
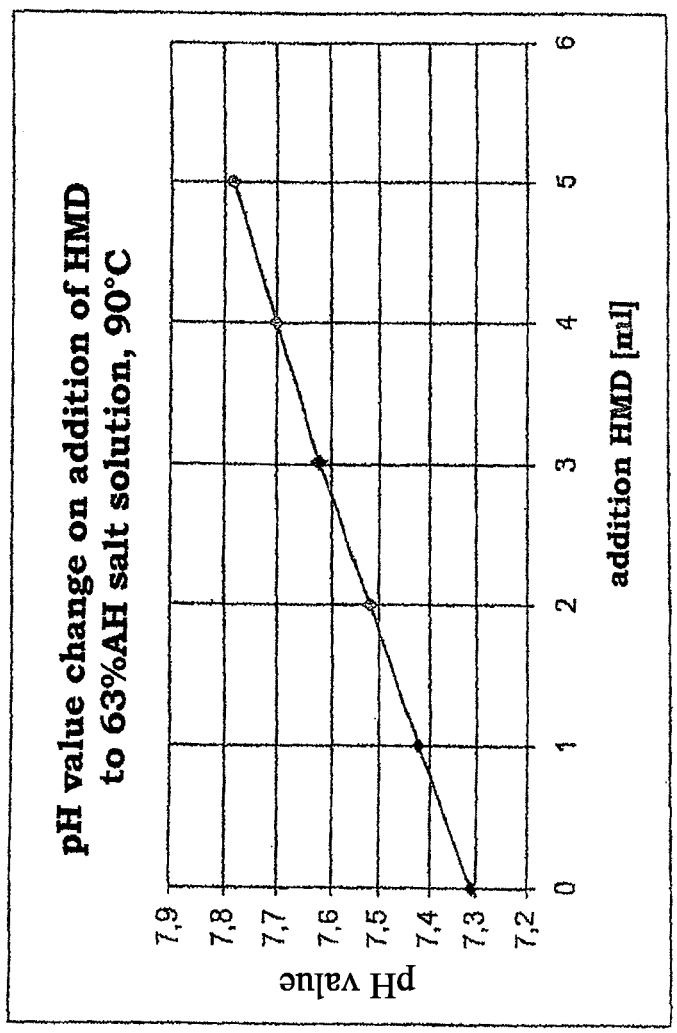
FIG. 3 shows the pH value change with the addition of HMD to a 63% AH salt solution at 90° C.

The tables reproduced in the subsequent FIGS. 1 to 3 relate to examples in which the production of an AH salt solution (hexamethylenediamine adipate) to form a 63% aqueous solution at 90° C. of solid adipic acid (ASS) and also liquid hexamethylenediamine solution (HMD) was implemented.

FIG. 1 now shows the dependency of the pH value upon the concentration of the AH salt at 90° C. As emerges from FIG. 1, no dependency of the pH value upon the concentration of AH salt has been established in the range, which is of interest from a technical process point of view, of 60 to 63% content of AH salt in the aqueous solution at 90° C.

In FIG. 2, the dependency of the pH value upon the temperature was examined.

As emerges from FIG. 2, a strong dependency of the pH value upon the temperature of AH salt solutions at 63% is revealed. In the case of the end temperature of 90° C., a pH value of the 63% aqueous AH salt solution of pH=7.31 was determined. In the temperature range of 70 to 90° C., which is of interest for the process, the pH value changes approximately linearly with the temperature. Per ° C. temperature increase, a reduction in the pH value by approx. 0.01 pH units is observed.

In FIG. 3, the pH value change with the addition of HMD to 63% AH salt solution at 90° C. is now represented. As emerges from FIG. 3, the addition of 1 ml HMD solution (corresponds to approx. 7 mmol), i.e. in an excess of HMD of 0.1% by mol relative to the 63% AH salt solution, leads to an increase in the pH value of approx. 0.01 pH units.

As emerges from the above-discussed FIGS. 1 to 3, adjustment of the molar ratio via a pH value measurement, with the proviso that the temperature is kept constant, is possible with adequate reliability.

Figure 4:
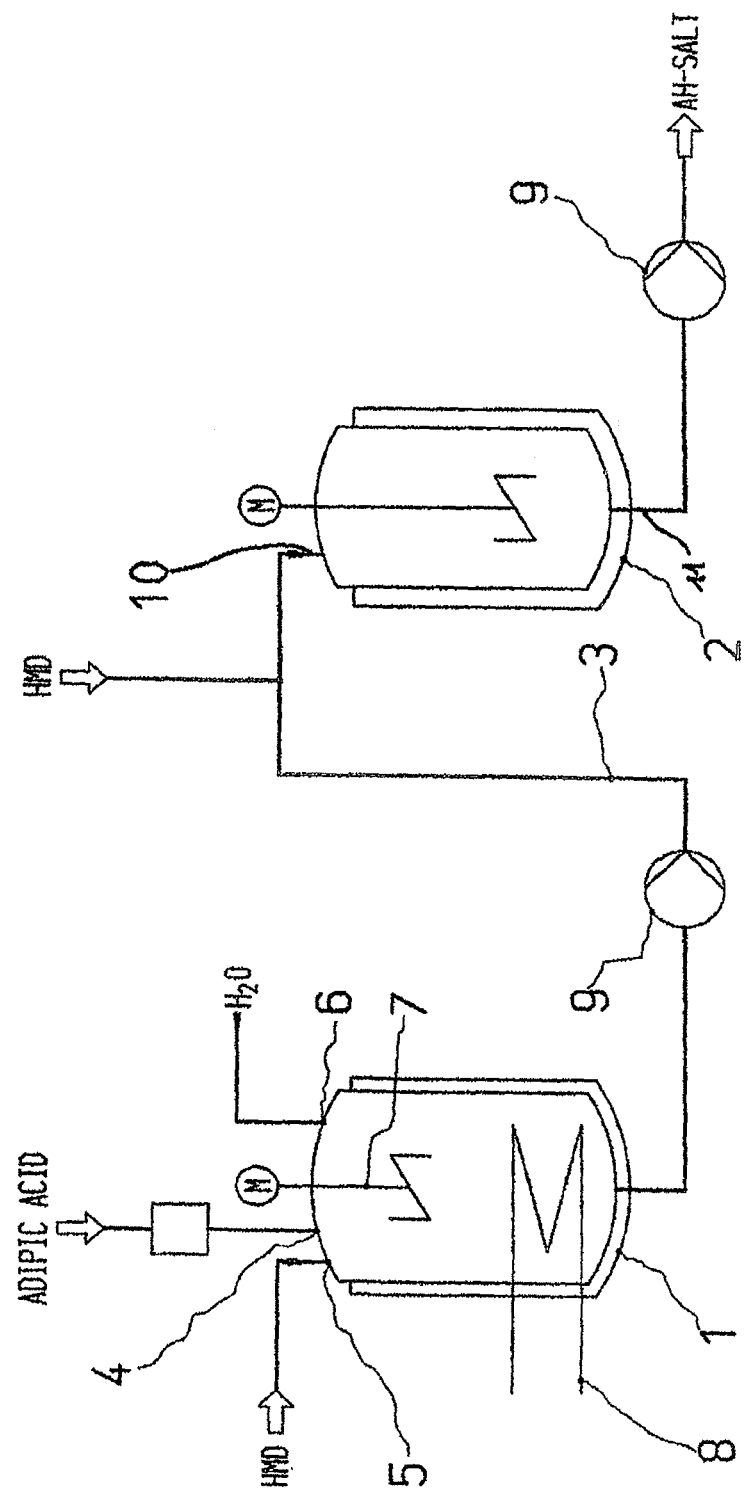
FIG. 4 shows schematically a device for implementing the method according to the invention.

In FIG. 4, a device according to the invention for implementing the method is now represented schematically.

The device according to the invention in the embodiment according to FIG. 4 consists of a stirred reactor 1 and a stirred reactor 2 which are connected to each other via a line 3. In the stirred reactor 1, at least one first feed point 4 which serves for supplying solid pulverulent adipic acid is provided. The adipic acid is thereby introduced into the stirred reactor 1 from a BigBag, not illustrated, or another suitable transport container via a corresponding metering device (likewise not illustrated). The stirred reactor 1 then has in addition a second feed point 5 which serves for supplying the diamine, in the case of the example here of hexamethylenediamine (HMD), and a further feed point 6 for the supply of water.

As emerges from FIG. 4, the stirred reactor according to the invention is provided with a stirring unit 7 and has in addition a heating or cooling spiral 8. In the stirred reactor 1, the metering, as described above, is undertaken in the substoichiometric ratio and the reaction course is controlled such that a concentration of approx. 63% in the stirred reactor 1 is adjusted. Via the line 3 and a pump 9, the salt solution is then transferred into the stirred reactor 2, here further hexamethylenediamine (HMD) being metered in via the feed point 10. The metered quantity is thereby based upon the pH value measurement (not illustrated) and is determined automatically. The stirred reactor 2 is then provided with an outflow 11 on the base so that the produced AH salt solution can be transported via a pump into a possibly present storage container.

The invention claimed is:

1. A method for the continuous production of an aqueous solution of salts by conversion of alkane dicarboxylic acids with 6 to 12 carbon atoms and alkane diamines with 6 to 12 atoms, having the following steps:
   a) a defined quantity of alkane dicarboxylic acid is metered as solid material through a metering device with a gravimetric throughflow measurement into a first reactor via at least one first feed point and a substoichiometric quantity of undiluted alkane diamine is metered in at at least a second feed point, and also, at the same time, water at at least one third feed point of the first reactor, for the production of an aqueous salt solution in the reactor,
   b) the formed salt solution is transferred continuously into a subsequently connected second reactor and
   c) making-up with the alkane diamine is effected in the second reactor, the stoichiometric ratios in the first and second reactor being adjusted by a pH value measurement at a constant temperature.

2. The method according to claim 1,
wherein, in the first reactor, a pH value of 6.0 to 7 is maintained and, in the second reactor, a pH value of 6.8 to 7.8.

3. The method according to claim 1,
wherein, in the first reactor, a stoichiometric ratio of alkane dicarboxylic acid to alkane diamine of 1:0.80 to 0.99 is maintained.

4. The method according to claim 1,
wherein, in the first reactor, the aqueous solution is maintained at a concentration of salts of alkane dicarboxylic acid and alkane diamines of 50 to 65% by weight.

5. The method according to claim 1,
wherein the conversion in the first and second reactor is implemented at temperatures of 70° C. to 120° C.

6. The method according to claim 1,
wherein the quantity of alkane diamine and water metered in in the first reactor is determined as a function of the quantity of introduced alkane dicarboxylic acid.

7. The method according to claim 1,
wherein a stirred reactor is used as first and second reactor.

8. The method according to claim 1,
wherein inert gas is supplied to the first and/or second reactor via at least one supply line.

9. The method according to claim 1, wherein the water and the inert gas for the first and/or second reactor are guided in a circulation.

10. The method according to claim 1,
wherein the alkane dicarboxylic acid is selected from the group consisting of adipic acid, octanedioic acid, azeleic acid, sebacic acid, decanedioic acid, dodecanedioic acid and mixtures hereof.

11. The method according to claim 1,
wherein the alkane diamine is selected from the group consisting of hexamethylenediamine, octamethylenediamine, decamethylenediamine, dodecamethylenediamine, bis(4-aminocyclohexyl)methane and bis(4-aminocyclohexyl)propane-2,2.

12. A device for the continuous production of an aqueous solution of salts by conversion of alkane dicarboxylic acids with 6 to 12 carbon atoms and alkane diamines with 6 to 12 carbon atoms, comprising:
a) a first reactor for the conversion of the alkane dicarboxylic acids with the alkane diamine, the first reactor having at least one first feed point for the alkane dicarboxylic acids, at least one second feed point for the alkane diamine and at least one third feed point for the water,
b) a second reactor which is connected to the first reactor and which has at least one additional feed point for the alkane diamine,
c) measuring devices for measuring the pH value of the aqueous solution of salts in the first and/or second reactor and
d) a control unit which controls making-up of the alkane diamine in the second reactor based on the measured pH value, wherein
the first and the second reactors are provided with a heating or cooling jacket or a heating or cooling device.

13. The device according to claim 12, wherein the second reactor is connected to a storage container.

14. The device according to claim 12,
wherein the first and second reactor are configured as stirred reactor.

15. The method according to claim 1, wherein, in the first reactor, a pH value of 6.0 to 7 is maintained and, in the second reactor, a pH value of 7.0 to 7.4.

16. The method according to claim 1, wherein, in the first reactor, a stoichiometric ratio of alkane dicarboxylic acid to alkane diamine of 1:0.85 to 0.99 is maintained.

17. The method according to claim 2, wherein, in the first reactor, the aqueous solution is maintained at a concentration of salts of alkane dicarboxylic acid and alkane of 50 to 65% by weight.

18. The method according to claim 1, wherein the conversion in the first and second reactor is implemented at temperatures of 80° C. to 95° C.

19. The method according to claim 2, wherein the quantity of alkane diamine and water metered in in the first reactor is determined as a function of the quantity of introduced alkane dicarboxylic acid.

20. A device for the continuous production of an aqueous solution of salts by conversion of alkane dicarboxylic acids with 6 to 12 carbon atoms and alkane diamines with 6 to 12 carbon atoms, comprising:
a) a first reactor for the conversion of the alkane dicarboxylic acids with the alkane diamine, the first reactor having at least one first feed point for the alkane dicarboxylic acids, at least one second feed point for the alkane diamine and at least one third feed point for the water,
b) a second reactor which is connected to the first reactor and which has at least one additional feed point for the alkane diamine,
c) measuring devices for measuring the pH value of the aqueous solution of salts in the first and/or second reactor and
d) a control unit which controls making-up of the alkane diamine in the second reactor based on the measured pH value;
wherein the second reactor is connected to a storage container.

* * * * *

UNITED STATES PATENT AND TRADEMARK OFFICE
CERTIFICATE OF CORRECTION

PATENT NO.        : 9,561,999 B2
APPLICATION NO.   : 14/131855
DATED             : February 7, 2017
INVENTOR(S)       : Siebecke et al.

Page 1 of 1

It is certified that error appears in the above-identified patent and that said Letters Patent is hereby corrected as shown below:

In the Claims

Claim 17, Lines 3-4, "alkane of 50 to 65% by weight" should read --alkane diamine of 50 to 65% by weight--.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*